United States Patent [19]

Oakes et al.

[11] 4,407,790

[45] Oct. 4, 1983

[54] METHOD OF CONTROLLING BLOAT USING NONIONIC SURFACTANTS

[75] Inventors: Thomas R. Oakes, Stillwater, Minn.; James L. Sadler, Cambridge, New Zealand

[73] Assignee: Economics Laboratory, Inc., St. Paul, Minn.

[21] Appl. No.: 305,395

[22] Filed: Sep. 25, 1981

[51] Int. Cl.$^3$ .................. A61K 31/74; A61K 31/08
[52] U.S. Cl. .................................. 424/78; 424/342
[58] Field of Search ............................ 424/342, 78

[56] References Cited

U.S. PATENT DOCUMENTS 3,248,289  4/1966  Shinozaki et al.
3,465,083  9/1969  Bartley et al. .................... 424/342
3,686,416  8/1972  Myer et al. ....................... 424/329
4,005,192  1/1977  Graham et al. ................... 424/342

FOREIGN PATENT DOCUMENTS 168364  9/1972  New Zealand.

OTHER PUBLICATIONS

Meyer et al.—J. Am. Science, vol. 34, No. 2, (1972), pp. 234–240.

*Primary Examiner*—Sam Rosen
*Attorney, Agent, or Firm*—Merchant, Gould, Smith, Edell, Welter & Schmidt

[57] ABSTRACT

A method for controlling bloat comprising administering to a ruminant nonionic surfactants comprising alkyl polypropyleneoxy-polyethyleneoxy polyethers.

10 Claims, No Drawings

METHOD OF CONTROLLING BLOAT USING NONIONIC SURFACTANTS

This invention relates to methods for controlling bloat in ruminants, e.g., cattle. More particularly, this invention relates to methods of controlling ruminant bloat using certain aliphatic polypropylene oxide polyethylene oxide block polyethers, also referred to as alkyl polypropyleneoxy-polyethyleneoxy polyethers.

Bloat is an affliction of ruminant livestock, particularly cattle and sheep, which occurs in many parts of the world. Ordinarily, bloat is characterized by an accumulation of gas and foam within the ruminoreticulium or first compartment of the ruminant stomach in sufficient quantity that the normal pressure within the rumen is exceeded and distension results. In its early stages, distension of the ruminant can be observed exteriorly as the swelling of the abdomen, particularly in the ruminant's left side. If continued untreated, the ruminant can suffer extreme abdominal distension, severe respiratory distress, prostration and ultimately, death.

Bloat (also called Tympanities) is believed to be due to the methane or carbon dioxide gas or foam generated during the microbial digestion in the ruminoreticulium. Generally, bloat is found to occur upon overeating of fermentive grasses, particularly leguminous plants such as alfalfa (e.g., bloat-inducing lucerne) and clover. A second, generally less severe type of bloat (called feedlot bloat) is found to occur when cattle are fed excessive amounts of high protein concentrates, e.g., in a feed-lot.

One factor which contributes to the perniciousness of bloat is that the elapsed time from its onset to the animal's death may be as little as ten to fifteen minutes. During this time period, an otherwise docile animal may become extremely nervous and unmanageable, thus making non-debilitating treatment very difficult. After the onset of bloat, the most reliable means of bloat treatment is the emergency rumenatomy, which requires a period of convalescence and exposes the animal to other infirmaties due to secondary causes.

The above difficulties in treating bloat (after its onset) have generated substantial interest in medicaments which can be used to prevent bloat. Among the materials which have been used in attempting to prevent bloat include a polymer composed of polypropylene glycol (molecular weight of 1,000 to 3,000) reacted with 5% to 30% ethylene oxide (U.S. Pat. No. 3,248,289), polyoxypropylene-polyoxyethylene polymers (molecular weight 1,900–2,000) having 25% to 40% polyoxyethylene (U.S. Pat. No. 3,465,083), aqueous alkyl aryl sulfonate sodium ("The Control of Experimental Legume Bloat with an Enzyme Inhibitor, Alkyl, Aryl Sulfonate Sodium", 9J.A.V.M.A. IU3 (1963), and salts of dimethyl dialkyl quaternary ammonium compounds (U.S. Pat. No. 3,686,416).

Nonionic surfactants have received considerable attention in the patent and technical literature for use in preventing (or treating) ruminant bloat. For example, the above-cited U.S. Pat. No. 3,465,083 patent describes the use of specific polyoxypropylene (PO) polyoxyethylene (EO) block polymers generally of the structure

HO(EO)—(PO)—(EO)H to prevent legume bloat. The above cited U.S. Pat. No. 3,248,289 patent also discloses the use of other polypropylene oxide-polyethylene oxide nonionic surfactants in preventing bloat. New Zealand provisional Patent Application No. 168,364 filed by the Commonwealth Scientific and Industrial Research Organization of Australia describes the use (in the treatment or prevention of bloat) of polyethoxy alkyl ether nonionic surfactants of the structure $$RO(CH_2CH_2O)_nH,$$

R being an alkyl chain (generally straight chain, alcohol-derived) and n being an integer having a preferred value of 9 to 30.

All of these previously used compositions suffer from various disadvantages of solubility, gel formation or lack of solubility thus leads to difficulty of use under actual farming conditions. For example, a 25% by weight aqueous solution of the alcohol ethoxylates described in the aforementioned New Zealand provisional patent application No. 168,364 forms a gel at room temperature. Further, the more hydrophobic the materials described in the aforementioned U.S. Pat. No. 3,465,083 (i.e., those having less ethylene oxide) are found to dissolve very slowly in cold water and often require the presence of a separate solubilizer. This is an important disadvantage because the more hydrophobic materials are more bloat-inhibiting.

The present invention overcomes the disadvantages of conventional materials and provides a specific class of nonionic surfactants (hereinafter described) which have excellent efficacy as bloat control or preventative agents. In addition, the materials of the present invention exhibit superior solubility characteristics which makes them particularly suitable in the generally preferred (and most reliable) method of bloat control or prevention, viz., drenching. Lastly, aqueous solutions throughout the entire concentration range of the present series of nonionic surfactants are motile liquids at room temperature which permits them to be used either in a preventative or curative fashion without the addition of viscosity-reducing agents (i.e., gallation does not occur).

SUMMARY OF THE INVENTION

Briefly, in one aspect, the present invention provides a class of nonionic surfactants which are particularly useful in the prevention or treatment of bloat. More particularly, the present invention provides a method of preventing or controlling bloat using nonionic surfactant of the structure $$RO(CH_2CHO)_x(CH_2CH_2O)_yH. \qquad I$$
$$\phantom{RO(CH_2}|}$$
$$\phantom{RO(CH_2CHO)_x(}CH_3$$

wherein R is a hydrophobic straight or branched, generally saturated aliphatic moiety having from about 6 to about 20 carbon atoms, x has a value of about 3 to 40, and y has a value of about 5 to 25. It is to be understood that x and y are average values of the number of moles of propyethylene oxide (PO) or ethylene oxide (EO) per aliphatic moiety (R). The bloat-inhibiting material of this invention might be represented by values of "x" and "y" which are not integral even though stoichiometry dictates individual surfactant molecules within the material would necessarily contain integral numbers of moles of PO and EO.

A mixture of nonionic surfactants of formula I as well as with other nonionic surfactants is also within the contemplation of this invention.

In a preferred aspect of this invention, R from formula I is a straight chain alkyl moiety having from 6 to about 17 carbon atoms, x has a value of about 4 to 33 and y has a value of about 6 to 24. R is normally derived from readily available long chain alcohols produced by the well-known Ziegler-type reaction. In preferred materials discussed below, R is actually a mixture of alkyl groups.

Because of their unexpectedly superior bloat-controlling efficacy, motility and solubility, a particularly preferred bloat-controlling material within the scope of formula I is the straight chain, generally alcohol-derived, nonionic surfactants wherein R has from 6 to 12 carbon atoms, x has a value of about 3 to 6 and y has a value 6 to 18.

In another aspect, this invention is the method of controlling bloat comprising administering (e.g., by drenching) to a bloat-susceptible ruminant or bloat-encountering ruminant a bloat-controlling amount of a nonionic surfactant of structure I. "Drenching" is the well-known technique of forcing a quantity (e.g., 30 to 40 milliliters) of a bloat-controlling material down the gullet of the ruminant. As the terms are used herein, "controlling" or "bloat-controlling" are intended to include prevention of bloat as well as cure of bloat once it has begun. Bloat may be said to be "controlled" when the symptoms of bloat (e.g., distension) are reduced and the danger or risk of loss of the animal is significantly reduced. Generally speaking a viable bloat-controlling composition must be capable of controlling bloat for a time-period exceeding twelve hours. This time-period is roughly the same as the time between milkings of especially bloat-susceptible lactating dairy cows.

In yet another aspect of this invention the nonionic surfactants of formula I may simply be added to the drinking water of the ruminant. The term "administering" is intended to include essentially any reliable technique for providing a bloat-controlling amount of the nonionic surfactants herein described to the ruminant's rumen.

DETAILED DESCRIPTION OF THE INVENTION

The nonionic surfactants of formula I above are particularly water soluble, even in cold or hard (i.e., high mineral content) water. This is important because an animal husbandman often doesn't have time to wait for slowly dispersing materials to dissolve. Furthermore, the materials of I have little tendency to form gels. This means an aqueous solution can be easily and quickly prepared.

As noted above, the present invention relates to the use of certain nonionic surfactants to control bloat. These nonionic surfactants are generally described by the structure designated I above. These materials are variously described as monofunctional polyols, hydrophobe-propoxylates-ethoxylates, or aliphatic-poly-propoxylates-polyethoxylates. It will be understood that any of these terms may be applicable to the compositions of the present invention, assuming the specified amounts of hydrophobe, propylene oxide and ethylene oxide have been reacted.

Formula I above, "R" may be generally described as an aliphatic hydrophobic moiety. This aliphatic moiety generally consists of organic hydrocarbon material preferably originating from commercially available linear alcohols. Generally speaking, R is an alkyl group having about 6-20 carbon atoms (e.g., a molecular weight in the range of about 70 to about 300), preferably having from about 6 to about 17 carbon atoms. Heteroatoms such as oxygen, sulfur, etc. are permissible provided the overall aliphatic moiety is hydrophobic, i.e., lacking in affinity for water. R is preferably linear, although a limited amount of branching is permissible. Linear alkyl groups are generally preferred because they tend to be more rapidly biodegradable and to exhibit greater control of bloat than corresponding branched isomers.

In formula I above, "R" is connected by means of an ether linkage

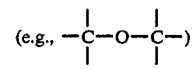

to a polypropylene oxide residue. This polypropylene oxide residue is added to the alkyl group in basic media by synthetic techniques which are well-known to one skilled in the art. The R-O-polypropylene oxide section of the molecules herein is obtained by the addition of about 3 to about 40 (preferably about 4 to about 33) moles of 1,2 propylene oxide to one mole of the "R" material. Synthesis of the molecules employed to control bloat herein is completed by the addition of from about 5 to 25 (preferably about 6 to about 24) moles of ethylene oxide per R-PO$_x$-intermediate. Again, synthesis is accomplished in basic media by well-known techniques.

It should be noted that EO and PO segments of the nonionic surfactants herein described are intended to be homogeneous ethylene oxide or propylene oxide "blocks". Thus, it is outside the contemplation of the present invention that a mixture of ethylene oxide and propylene oxide be condensed on an appropriate hydrophobic moiety.

In his paper entitled "Surface Active Agents in the Rumen", R. H. Laby of the Commonwealth, Science and Industrial Research Organization of Australia discusses some of the factors important in controlling bloat. Among the factors discussed are detergency (i.e., the ability of a surfactant to clean and remove soil and hydrophobe-lipophobe balance (HLB). As described by Laby, materials which tended to control bloat for a sufficient period of time (e.g., 12 hours) had good detergency properties and HLB's in the range of 14 to 17. It should be noted that while criteria may be important, bloat control is a very empirical science. The mere fact that a given material meets either or both of the above criteria does not mean the material will control bloat. The only truly trustworthy critereon which can be applied to a given proposed bloat remedy is whether the material works under field conditions.

The bloat-controlling nonionic surfactants of the present invention may be sold as 100% active (i.e., undiluted). To reduce occasional slight opacity in a larger quantity of surfactant, 95% solution (5% water) may be prepared. Two or more of the nonionic surfactants may be mixed and also sold without dilution. If a 100% active material or mixture is sold, then the purchaser would dilute the concentrate (e.g., with water to about 20% by weight) to produce the composition actually administered to the ruminants. Alternatively, the non-ionic surfactants herein described may be diluted with water prior to sale. Either of these approaches have advantages in terms of ease of administration or shipping costs. Further, these materials may be incorporated into solid, fluid, or gelled media which are fed to ruminants. Various other elements, hormones or other materials conventionally administered to ruminants to control growth rate, diet enhancement or disease prevention may be mixed with the materials of the present invention and added to the ruminant's food.

Further details of the performance of the bloat-controlling materials of the present invention and methods by which they may be employed are described in the following examples. These examples are intended to be illustrative and should not be construed so as to limit this invention.

EXAMPLE 1

A preliminary bloat control trial was carried out on a dairy involving three nonionic surfactants described in Table I. Cattle known to have a tendency to bloat were selected from the herd and were drenched with 40 mls of a 20% by weight solution of the test surfactant in water. Cattle were free grazing lucerne alfalfa and bloat was quite severe, it being incompletely controlled with conventional drenches. Surfactant "A" in Table I did not appear to provide bloat control immediately after milking but did later exhibit limited bloat suppression. Surfactants "B" and "C" (in Table I) showed excellent short and long-term bloat suppression.

TABLE I

| Surfactant number | "R" | x | y |
|---|---|---|---|
| A. | $C_8/C_{10}$* | 6 | 7 |
| B. | $C_8/C_{10}$ | 6 | 9 |
| C. | $C_{10}/C_{14}$** | 3 | 9.3 |
| D. | $C_8/C_{10}$ | 6 | 9 |
| E. | $C_{10}/C_{14}$ | 6 | 12 |
| F. | $C_8/C_{10}$ | 6 | 18 |
| G. | $C_8/C_{10}$ | 6 | 18 |
| H. | $C_{10}/C_{14}$ | 3 | 12 |
| I. | $C_{10}/C_{14}$ | 3 | 15 |
| J. | $C_{10}/C_{14}$ | 3 | 18 |

*a 50/50 percent by weight of a $C_8/C_{10}$ straight chain alcohol comercially available under the trade designation "ALFOL" 810 from Continental Oil Company.
**a mixture of straight chain alcohols having approximately equal amounts of $C_{10}$, $C_{12}$ and $C_{14}$ alkyl chains commercially available under the trade designation "ALFOL" 1014 from Continental Oil Company.

EXAMPLE 2

A further preliminary trial was carried out on the same herd using a wider range of surfactants designated D-J in Table I. Once again several selected animals were drenched with a 40 ml dose of a 20% solution of each of the test surfactants. Observations over a severe bloat period showed that all products controlled bloat, i.e., they reduced the incidence and severity of bloat and reduced animal distress without significant change in milk yield. Surfactant "G" was not as active as some of the other materials and Surfactant "I" gave limited initial bloat control.

EXAMPLE 3

A larger scale trial was imitiated using $C_8/C_{10}$—$PO_6$—$EO_9$—H and $C_{10}/C_{14}$—$PO_3$—$EO_9$—H. These materials have great motility and dissolve very readily to virtually any concentration in water providing considerable advantage in practical use. The materials were premixed as a 18% solution in water. Trials were performed on a dairy farm at Whakatane, New Zealand grazing normal pasture and on a dairy farm at Reparoa, New Zealand grazing lucerne alfalfa and normal pasture. On each farm 20 animals were selected from the herd and divided into two groups of ten. The animals selected were marked accordingly for the duration of the trial.

In each case one group of ten animals was dosed with the test product and the other group was dosed with conventional bloat remedies available under the trade designation "Bloatenz" from Economics Laboratory, Inc., New Zealand. "Bloatenz 2 in 1" bloat remedy was employed on the farm in Whakatane and "Bloatenz L" bloat remedy was employed on the farm in Reporoa, New Zealand. These materials are polyethylene oxide-polypropylene oxide polyether-based bloat remedies. Both "Bloatenz" bloat inhibitors were mixed to 33% by weight in water solution. Animals then were drenched with the same volumes of mixed products thus providing a greater quantity of "Bloatenz" inhibitor than the test products because of its higher concentration.

After one week the product given to the test groups was changed so that the group receiving the test product in the first week received the "Bloatenz" bloat remedy (by drench) in the second and vice versa.

The fourteen day bloat scores for the materials tested are summarized in Table II:

TABLE II

| SURFACTANT | BLOAT SCORE* |
|---|---|
| On Normal Pasture | |
| $C_8/C_{10}$—$PO_6$—$EO_9$—H | 28 |
| "Bloatenz 2 in 1" | 73 |
| $C_{10}/C_{14}$—$PO_3$—$EO_9$—H | 27 |
| "Bloatenz 2 in 1" | 23 |
| On Lucerne | |
| $C_8/C_{10}(PO)_6$—$EO_9$ | 5 |
| "Bloatenz L" | 21 |
| $C_{10}/C_{14}(PO)_2$—$(EO)_9$ | 2 |
| "Bloatenz 2 in 1" and "Bloatenz L" | 7 |

*Bloat score is the total of the Johns bloat score (see Example 4) for the group of ten animals over the two week period of the trial.

The incidence of predictable bloat was less during the third and fourth week on this farm making comparisons less precise. However, indications were that $C_8/C_{10}$—$PO_6$—$CO_9$—H is superior to Bloatenz 2 in 1 and $C_{10}/C_{14}$—$PO_3$—$EO_9$—H are much the same in controlling normal pasture bloat.

Weeks one and two were on young high bloat-producing lucerne. Week three and four were mainly normal pasture.

EXAMPLE 4

Several tests were undertaken to test the efficacy of surfactants of the present invention in relieving an already bloated cow.

1. In a dairy herd in Whakatane, New Zealand, one cow was intentionally not drenched after milking in the evening or the following morning. Approximately two hours after milking she was examined. At this time she was experiencing bloat to stage three to four on the Johns system and was somewhat distressed. (The Johns System of bloat scoring was developed by Dr. A. T. Johns, formerly of the New Zealand Agriculture and Fisheries. It is a relatively simply visual assessment of the severity of bloat, all assessments being made by viewing the animal from behind. The stages are as follows:

1. Very slight distension on left flank;
2. Increased distension on left, slight distension on right flank, moderate bloat;
3. Very distended on left, full and firm right flank, animal urinates and defaecates frequently, milk production is reduced, severe bloat;
4. Both flanks are very distended and level with backbone, animal is distressed, attempts to kick itself, and is unable to remain lying or standing still, violent tail movements, dangerous bloat;
5. Death.)

The cow was drenched with only 40 mls of a 18% solution of $C_8/C_{10}$—$PO_6$—$EO_9$—H and was confined in a bail for observation. Within seven minutes the cow's bloat symptoms had subsided to a Johns two level. She was then walked back to the pasture by which time all signs of bloat had disappeared.

2. In a Reparoa, New Zealand herd 15 dry cows were given free access to a large paddock of young grass and clover. Within two hours they were severely bloated and in fact some had difficulty entering the shed. All were drenched with doses of from 20 to 60 mls of 18% solution of $C_8/C_{10}$—$PO_6$—$EO_9$—H. Once again symptoms showed signs of reduction within seven minutes and all signs of bloat disappeared within one-half hour. Animals remained bloat free for 24 hours after at which time the evaluation ceased.

3. Two other tests were made on farms in the Waikato, New Zealand area and one at Galatea, New Zealand on naturally bloated cows with the same results when using $C_8/C_{10}$—$(PO)_6$—$(EO)_9$—H.

What is claimed is:

1. A method for the prevention or treatment of bloat in ruminants comprising the step of administering to a bloat-susceptible ruminant a bloat-controlling amount of a composition comprising nonionic surfactant of the structure

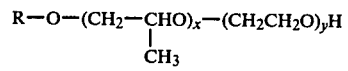

wherein R is an aliphatic, hydrophobic moiety, having about 6 to about 20 carbon atoms, x has a value of about 3 to about 40, y has a value of about 5 to 25.

2. A method according to claim 1 wherein the composition further comprises up to about 95 percent by weight water.

3. A method according to claim 1 wherein the composition is orally administered to ruminants.

4. A method according to claim 1 wherein the composition is administered by drenching the ruminant.

5. A method according to claim 1 wherein R is a linear alkyl chain.

6. A method according to claim 1 wherein x has a value of about 4 to about 33.

7. A method according to claim 1 wherein y has a value of about 6 to about 24.

8. A method for controlling bloat in ruminants comprising the steps of mixing a nonionic surfactant of the structure

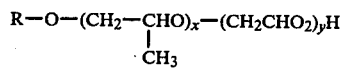

wherein R is an aliphatic, hydrophobic moiety, having about 6 to about 20 carbon atoms, x has a value of about 3 to about 40, y has a value of about 5 to about 25 with from about 10 to about 90% by weight water; and administering said mixture to a bloat-susceptible ruminant in sufficient quantity to suppress or inhibit the formation of bloat therein.

9. A method according to claim 8 wherein x has a value in the range of about 4 to about 33.

10. A method according to claim 8 wherein y has a value in the range of about 6 to about 24.

* * * * *